(12) United States Patent
Yoo et al.

(10) Patent No.: US 7,151,301 B2
(45) Date of Patent: Dec. 19, 2006

(54) SENSITIVITY ENHANCED BIOMOLECULE FIELD EFFECT TRANSISTOR

(75) Inventors: Kyu-tae Yoo, Seoul (KR); Geun-bae Lim, Pohang-si (KR); Joon-ho Kim, Seongnam-si (KR); Kak Namkoong, Seoul (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/057,642

(22) Filed: Feb. 14, 2005

(65) Prior Publication Data

US 2005/0199917 A1    Sep. 15, 2005

(30) Foreign Application Priority Data

Feb. 20, 2004    (KR)    .................. 10-2004-0011321

(51) Int. Cl.
*H01L 29/76*    (2006.01)

(52) U.S. Cl. ................................. 257/401; 257/253

(58) Field of Classification Search ............. 257/401, 257/253; 324/71.5; 436/806; 438/284, 438/286
See application file for complete search history.

(56) References Cited

U.S. PATENT DOCUMENTS

| | | | |
|---|---|---|---|
| 3,615,934 A | 10/1971 | Bower | 148/186 |
| 3,624,466 A | 11/1971 | Schnable | 317/235 |
| 4,238,757 A | 12/1980 | Schenck | 357/25 |
| 4,288,806 A * | 9/1981 | Ronen | 257/409 |
| 4,322,680 A | 3/1982 | Janata et al. | 324/71 SN |
| 4,777,019 A | 10/1988 | Dandekar | 422/68 |
| 4,881,109 A * | 11/1989 | Ogawa | 257/253 |
| 5,034,192 A * | 7/1991 | Wrighton et al. | 422/82.02 |
| 5,140,393 A * | 8/1992 | Hijikihigawa et al. | 257/252 |
| 5,304,836 A * | 4/1994 | Lao et al. | 257/399 |
| 5,309,085 A * | 5/1994 | Sohn | 257/253 |
| 5,431,883 A * | 7/1995 | Barraud | 422/82.01 |
| 5,445,920 A * | 8/1995 | Saito | 430/311 |
| 5,466,348 A | 11/1995 | Holm-Kennedy | 204/153.1 |
| 5,543,024 A * | 8/1996 | Hanazato et al. | 257/253 |
| 5,668,392 A * | 9/1997 | Huang et al. | 257/340 |
| 5,846,708 A | 12/1998 | Hollis et al. | 435/6 |
| 5,965,925 A * | 10/1999 | Kornachuk et al. | 257/401 |
| 6,140,687 A * | 10/2000 | Shimomura et al. | 257/401 |
| 6,203,981 B1 | 3/2001 | Ackley et al. | 435/6 |

(Continued)

FOREIGN PATENT DOCUMENTS

JP    05048095 A *    2/1993    ................. 257/401

(Continued)

OTHER PUBLICATIONS

European Search Report; Application No. 0500298.0—2204 PCT/; Date of Completion: Jul. 6, 2005.

*Primary Examiner*—Eugene Lee
(74) *Attorney, Agent, or Firm*—Cantor Colburn LLP (57) ABSTRACT

There is provided a biomolecule FET enhancing a sensitivity. The biomolecule FET includes a substrate, first and second impurity regions formed on both sides of the substrate, and doped with impurities of a polarity opposite to that of the substrate, a gate formed on the substrate and being in contact with the first and second impurity regions, and a probe biomolecule attached to the gate. A region of the gate adjacent to the first impurity region is wider than a region thereof adjacent to the second impurity region. A density of the probe biomolecule attached to the surface of the gate is increased, and when detecting a level of hybridization of the probe biomolecule and the target biomolecule, its sensitivity is improved.

11 Claims, 6 Drawing Sheets

U.S. PATENT DOCUMENTS

| | | | |
|---|---|---|---|
| 6,274,915 B1 | 8/2001 | Krishnan et al. | 257/407 |
| 6,699,667 B1 * | 3/2004 | Keen | 435/6 |
| 6,740,911 B1 * | 5/2004 | Chou et al. | 257/288 |
| 6,864,178 B1 * | 3/2005 | Kim | 438/692 |
| 2005/0116295 A1 * | 6/2005 | Mayer et al. | 257/354 |

FOREIGN PATENT DOCUMENTS

| | | | |
|---|---|---|---|
| JP | 05048095 A | * | 4/2000 |

* cited by examiner

SENSITIVITY ENHANCED BIOMOLECULE FIELD EFFECT TRANSISTOR

BACKGROUND OF THE INVENTION

This application claims the priority of Korean Patent Application No. 10-2004-0011321, filed on Feb. 20, 2004, in the Korean Intellectual Property Office, the disclosure of which is incorporated herein in its entirety by reference.

1. Field of the Invention

The present invention relates to a sensitivity enhanced biomolecule field effect transistor (FET), and more particularly, to a biomolecule FET enhancing sensitivity when detecting a biomolecule by improving a structure of a transistor-based biomolecule FET.

2. Description of the Related Art

Among sensors designed to detect a biomolecule using an electrical signal, there is a TR-based biosensor having a transistor structure. The biosensor is manufactured through a semiconductor manufacturing process, and has advantages in that the electrical signal is quickly converted and inoculation of IC and MEMS is simplified. However, since the biosensor has a lower confidence in a ratio of signal-to-noise (SNR) which is an important variable in the biosensor, various efforts to improve the ratio are in progress.

To detect a biological reaction using an FET is disclosed in U.S. Pat. No. 4,238,757 (1980), in which it refers to a biosensor for detecting a current and claims protein among biomolecules, and which a reaction between an antigen and an antibody is detected by use of a change in a semiconductor inversion layer due to a variation of a surface-charge concentration. U.S. Pat. No. 4,777,019 (1986) discloses an FET for detecting a level of hybridization between biological monomers attached onto a surface of a gate and complementary monomers. U.S. Pat. No. 5,846,708 (1998) discloses a method for detecting a level of hybridization using light attenuation caused by a biomolecule provided with a charged coupled device (CCD). U.S. Pat. Nos. 5,466,348 and 6,203,981 disclose to improve the SNR using a thin film transistor (TFT) associated with a circuit.

The TFT, it can lower the costs in relation to a transistor formed on a silicon substrate. Also, it is possible to manufacture an array of chips by enlarging a surface area of the substrate to improve a degree of integration. Use of the FET as the biosensor results in an economical, quick and simplified inoculation of IC/MEMS. Since such a conventional biomolecule FET represents the SNR when actually performing a test, it has disadvantages of lowering reproducibility and precision.

Figure 1A:
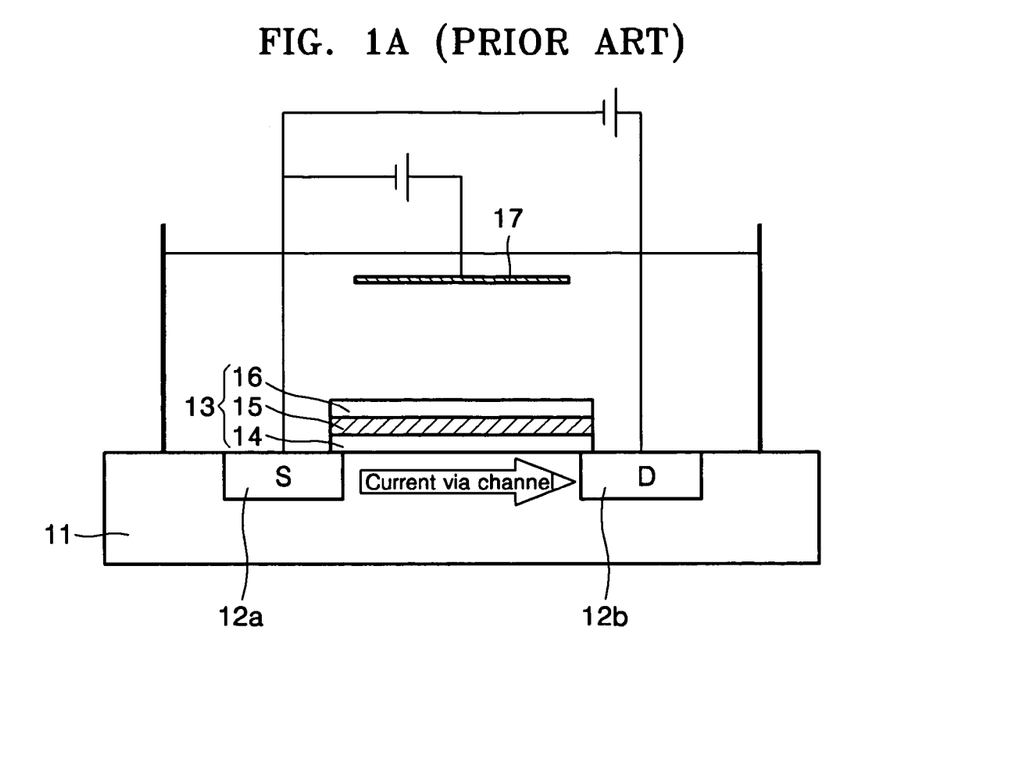
FIG. 1A is a cross-sectional view of a conventional biomolecule FET.

FIG. 1A is a cross-sectional view of a conventional biomolecule FET. A source 12a and a drain 12b are formed on both sides of an n-type or p-type doped substrate 11. A gate 13 is formed on the substrate 11 to be in contact with the source 12a and the drain 12b. The gate 13 generally includes an oxide layer 14, a poly-silicon layer 15, and a gate electrode layer 16, and probe biomolecules are attached to the gate electrode layer 16. The probe biomolecules are coupled by a desired target biomolecule and hydrogen bond, and is detected using an electrical method to measure a coupling degree of the probe and the target biomolecule.

Figure 1B:
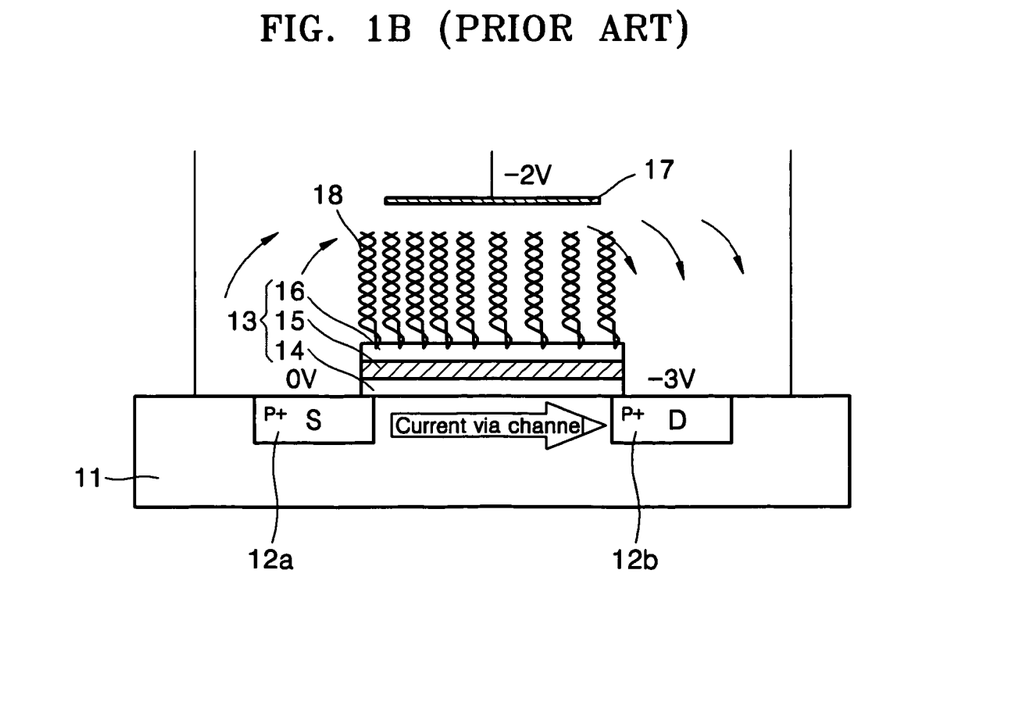
FIG. 1B is a view illustrating a probe attached to a surface of a gate electrode and a target biomolecule coupled to the probe biomolecule.

FIG. 1B shows a probe 18 attached to a surface of the gate electrode 16 and the target biomolecule coupled to the probe 18. According to the biomolecule FET using a reference electrode 17, there is a difference in electric potential between the source 12a and the reference electrode 17, and the drain 12b and the reference drain 17. Biomolecules charged by electrokinetic force under an electric field are not uniformly distributed on the gate 13 between the source 12a and the drain 12b, and the distribution is varied depending upon a position. For example, in DNA having a negative electric charge, when immobilization of a probe DNA and hybridization of a target DNA are detected using a p-type FET, the immobilization of a probe DNA and the hybridization of a target DNA are high on the gate 13 adjacent to the source 12a under the influence of a strong electric field between the source 12a and the reference electrode 17. Consequently, the charge density of the biomolecule attached to the surface of the gate 13 directly affects a variation of the FET current. Therefore, since the charge density on the gate 13 is varied depending upon the position, there is needed for a method of increasing the SNR of the biomolecule FET by altering the structure of the gate 13.

SUMMARY OF THE INVENTION

The present invention provides a biomolecule FET for enhancing sensitivity when detecting a biomolecule by improving a structure of a transistor-based biomolecule FET.

According to an aspect of the present invention, there is provided a transistor based biomolecule FET including a substrate, first and second impurity regions formed on both sides of the substrate and doped with impurities of a polarity opposite to that of the substrate, a gate formed on the substrate and being in contact with the first and second impurity regions, and a probe biomolecule attached to the gate, wherein a region of the gate adjacent to the first impurity region is wider than a region thereof adjacent to the second impurity region.

The gate and the first impurity region may enclose the second impurity region in a circular shape.

The biomolecule FET may further comprise a reference electrode formed on the gate for detecting a level of hybridization of the probe biomolecule and a target biomolecule.

If the substrate is doped with an n-type, the first impurity region and the second impurity region are doped with a p-type.

The biomolecule may include DNA, RNA, and protein.

The gate may include an oxide layer, a poly-silicon layer formed on the oxide layer, and a gate electrode layer formed on the poly-silicon layer.

According to another aspect of the present invention, there is provided a transistor-based biomolecule FET including a substrate, first and second impurity regions formed on both sides of the substrate, and doped with impurities of a polarity opposite to that of the substrate, a gate formed on the substrate and being in contact with the first and second impurity regions, and a probe biomolecule attached to the gate, wherein the gate is in contact with an outer, upper portion of the second impurity region to enclose a region of the second impurity region, and the first impurity region encloses an outer, lower portion of the circular gate.

The biomolecule may further comprise a channel having a desired width between the first impurity region and the second impurity region.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Reference will now be made in detail to a biomolecule FET according to the present invention.

Figure 2:
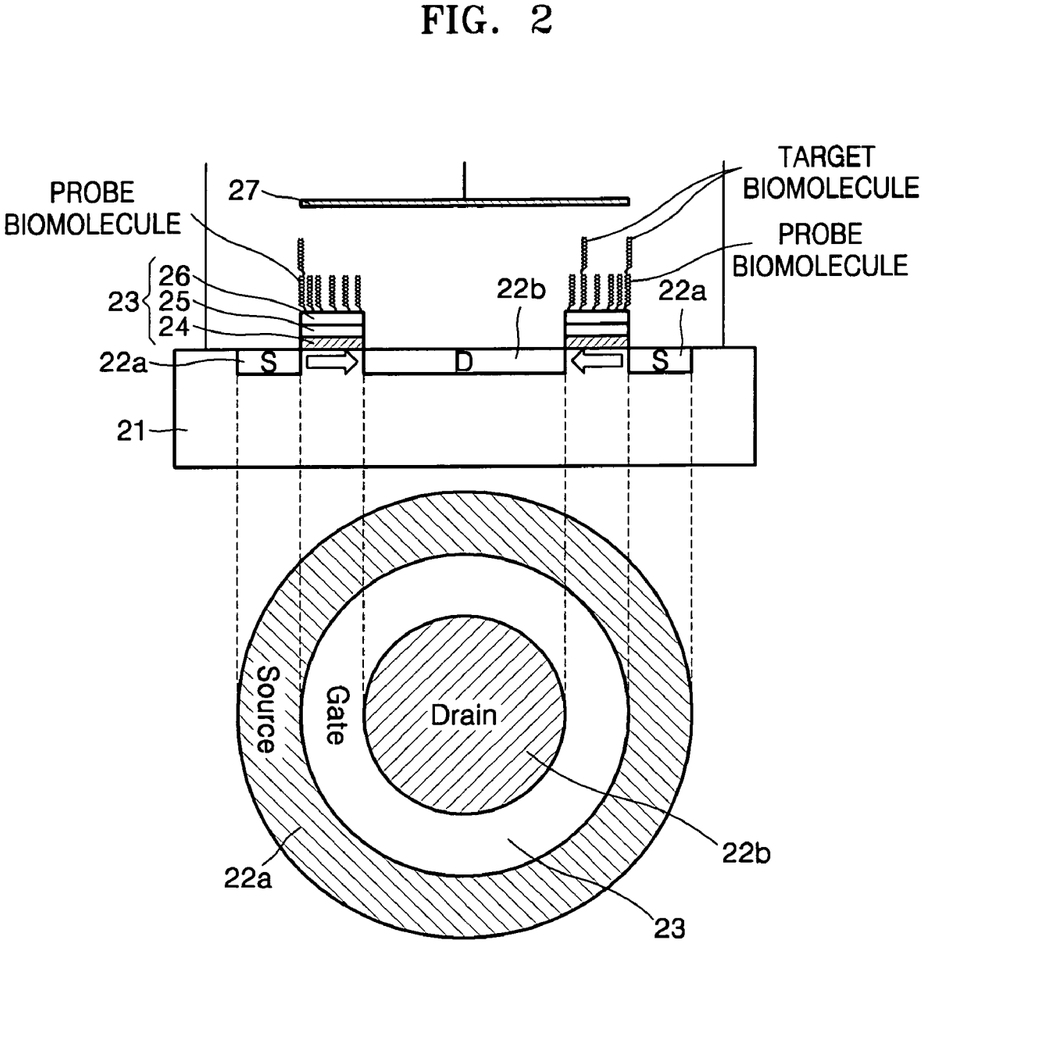
FIG. 2 is a view illustrating a circular biomolecule FET according to the present invention.

FIG. 2 is a view illustrating the biomolecule FET according to the present invention. The biomolecule FET is characterized in that a region where a first impurity region 22a (source) is in contact with a gate 23 is wider than a region where a second impurity region 22b (drain) is in contact with the gate 23. Preferably, the biomolecule FET has a circular construction in which the gate 23 and the first impurity region 22a enclose the second impurity region 22b. The gate 23, for example, includes an oxide layer 24, a poly-silicon layer 25, and a gate electrode layer 26.

Referring to FIG. 2, the first impurity region 22a and the second impurity region 22b are formed on a substrate 21. If the substrate 21 is doped in an n-type, the first impurity region 22a and the second impurity region 22b are doped in a p-type. The gate 23 is formed on the substrate 21 in a center of the first impurity region 22a and the second impurity region 22b. At this time, the biomolecule FET has a circular construction in which the gate 23 and the first impurity region 22a enclose the second impurity region 22b. Seeing a top view of the biomolecule FET according to the present invention, it can be seen that the gate 23 and the first impurity region 22a enclose the second impurity region 22b.

In the case where the gate 23 and the first impurity region 22a are adapted to enclose the second impurity region 22b, the first impurity region 22a is formed on both sides of the second impurity region 22b, with a channel having a desired width formed between the regions 22a and 22b, as shown in FIG. 2. It will be noted that the first impurity region 22a formed on both sides of the second impurity region 22b is a unitary region with an electrical connection to each other. An upper portion of the second impurity region 22b is in contact with the gate 23, while an outer, lower portion of the gate 23 is in contact with the first impurity region 22a, so that its cross section is a structure of a typical transistor.

The structure shown in FIG. 2 assists in solving a drawback of the transistor-type biomolecule FET employing the reference electrode 27 in an electrolyte solution.

In the case of the conventional biomolecule FET as shown in FIG. 1A, there is a difference in an immobilization density of the probe between a region adjacent to the first impurity region 12a and a region adjacent to the drain 12b in a surface of the gate 13. According to the biomolecule FET according to the present invention in FIG. 2, however, a surface area of a region adjacent to the first impurity region 22a is relatively widened in the gate 23, which can increase an immobilization density of the probe. A charge density of the charged biomolecule attached to the surface of the gate 23 results in a change of a threshold voltage or drain-source current (IDS). Consequently, if the density of the charged biomolecule attached to the surface of the gate 23 is increased, an SNR of the biomolecule FET is also increased.

Figure 3A:
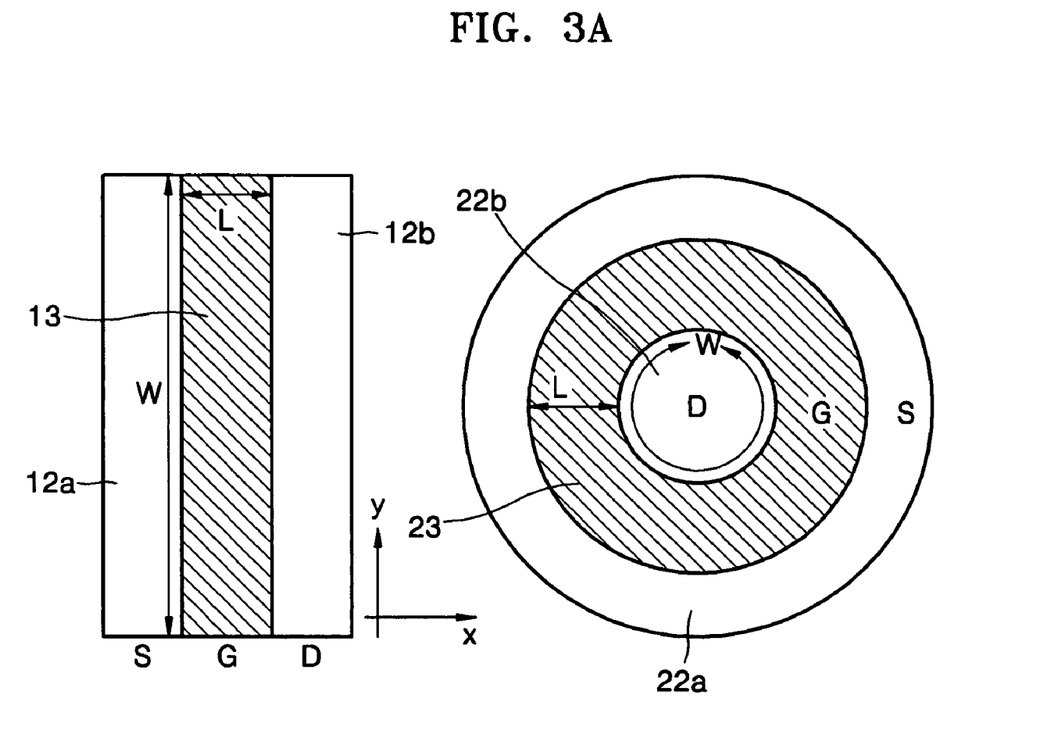
FIG. 3A is a top view illustrating a first impurity region, a gate and a second impurity region of a circular biomolecule FET according to the present invention and a conventional rectangular biomolecule FET.

FIG. 3A is a top view illustrating the first impurity region 22a, the gate 23, and the second impurity region 22b of the circular biomolecule FET according to the present invention and a conventional rectangular biomolecule FET. If a probe biomolecule is attached to an upper portion of the gate 23, it is possible to see a difference of the immobilization density with respect to a surface region of the gate 23. An attaching rate of the probe biomolecule in a hatched region on the surface of the gate 23 is higher than that in a white region on the surface of the gate. Specifically, the attaching rate of the probe biomolecule on the surface of the gate 23 adjacent to the first impurity region 22a is higher than that on the region adjacent to the second impurity region 22b.

In the FET, a ratio of W/L (a ratio of a width to a length; WLR) of the gate 23 is an important factor in determining an electrical characteristic (I-V characteristics) of the device. Accordingly, even though the width and the length of the gate 23 are different from each other, the device presents the same electrical characteristic if the ratio of W/L is equal.

Figure 3B:
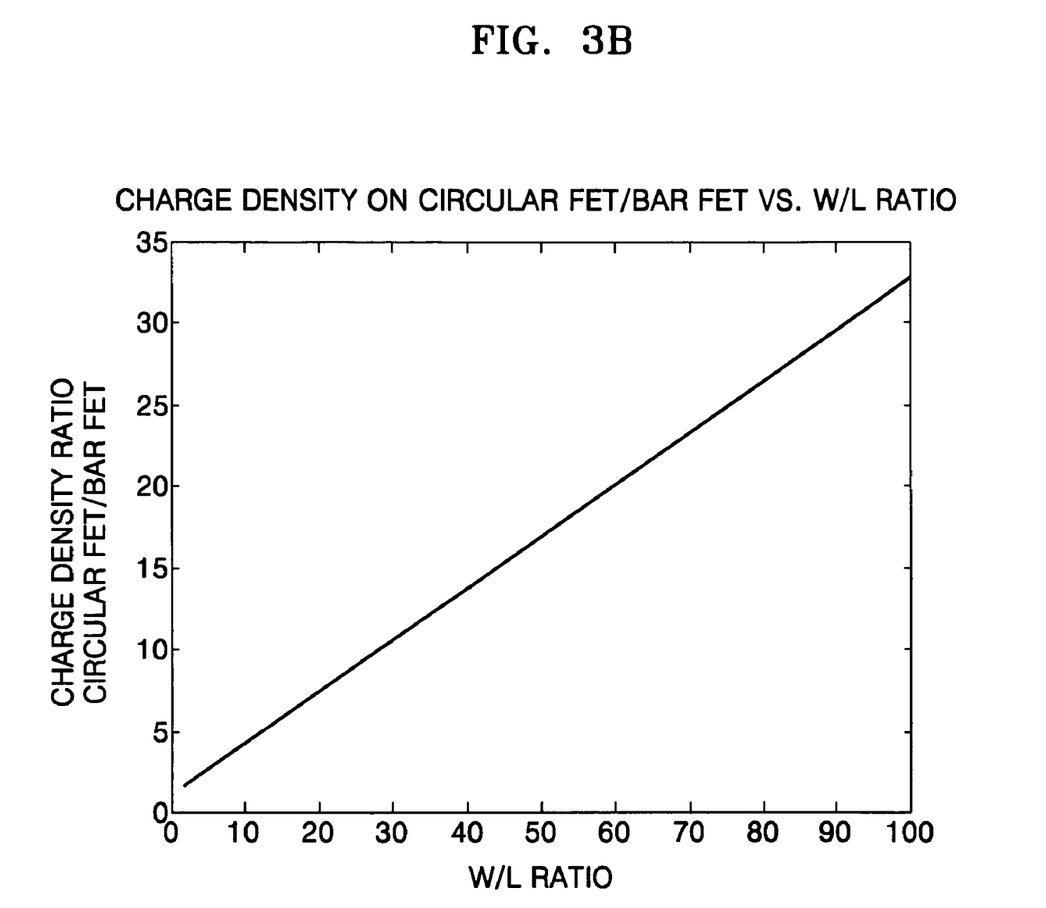
FIG. 3B is a graph depicting a ratio of charge density and a WLR of a circular biomolecule FET according to the present invention and a conventional rectangular biomolecule FET shown in FIG. 3A.

FIG. 3B is a graph depicting a ratio of charge density and the WLR of the circular biomolecule FET according to the present invention and a conventional rectangular biomolecule FET shown in FIG. 3A. Referring to FIG. 3B, it would be understood that if the WLR of the biomolecule FET according to the present invention is equal to that of the conventional biomolecule FET, the charge density of the biomolecule FET according to the present invention is higher than that of the conventional biomolecule FET.

In order to verify the above fact, seeing the case where the WLR is 20, the charge density of the biomolecule FET according to the present invention is about 7.3 times as high as that of the conventional biomolecule FET. If the WLR is up to 10, there is no remarkable difference. If the ratio of W/L is above 30, the ratio of the charge density is gradually increased to be above 10. If the WLR is small, there is no remarkable difference between the region adjacent to the first impurity region 22a and the region adjacent to the second impurity region 22b. If the WLR is high, since a width of the gate 23 is formed in a small size, the region adjacent to the first impurity region 22a is widened relative to the region adjacent to the second impurity region 22b. Accordingly, a density of the probe biomolecule attached to the surface of the gate 23 is increased, an amount ratio of the target biomolecule to be attached to the surface is also increased.

The biomolecule FET is classified as a p-type and an n-type depending upon a kind of a channel, such as a metal oxide silicon field effect transistor (MOSFET). When the p-type biomolecule FET is used to detect a negatively charged biomolecule, it is possible to apply a negative bias to a reference electrode to derive coupling of the probe and the target biomolecule in comparison with a source of the first impurity region. Consequently, it can be applied to the negatively charged biomolecule and the p-type biomolecule FET, and it can be similarly applied to a positively charged biomolecule and the n-type biomolecule FET.

As shown in FIG. 3B, according to the biomolecule FET according to the present invention having the circular gate, a threshold voltage of the transistor is decreased due to the increased density of the attached probe biomolecule, relative to the conventional biomolecule FET having the rectangular gate. Therefore, a current value is increased to increase a ratio of S/N.

Figure 4A:
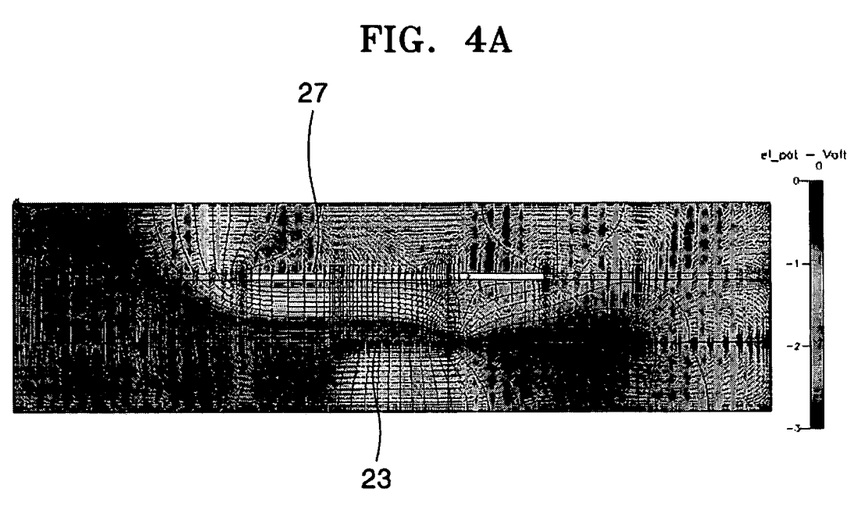
FIG. 4A is a view depicting an electrical field formed in a reference electrode and a gate region of a circular biomolecule FET, when a probe DNA is attached to the gate of the circular biomolecule FET.
Figure 4B:
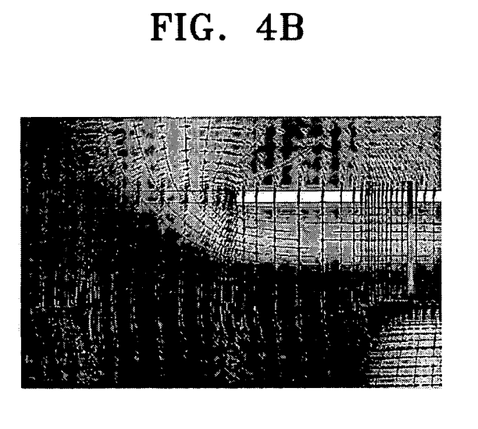
FIG. 4B is a view enlarging a reference electrode and a gate adjacent to the first impurity region (source) in FIG. 4A.
Figure 4C:
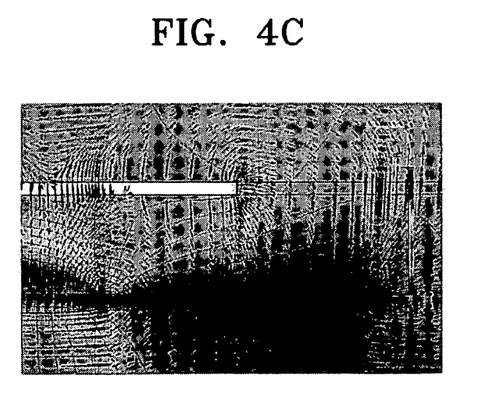
FIG. 4C is a view enlarging a reference electrode and a gate adjacent to the second impurity region (drain) in FIG. 4A.

FIG. 4A is a view depicting test results on an electrical field formed in the reference electrode and the region of the gate 23 of the circular biomolecule FET, when a probe DNA is attached to the gate of the circular biomolecule FET. FIG. 4B is a view of the enlarged reference electrode and gate adjacent to the first impurity region (source) in FIG. 4A. FIG. 4C is a view of the enlarged reference electrode and the gate adjacent to the second impurity region (drain) in FIG. 4A.

When the bias voltage is applied between the reference electrode and the biomolecule FET of the present invention, the electrical field is formed as shown in FIG. 4A. The electrical field applied to the surface of the gate adjacent to the first impurity region acts as an attraction to draw the negatively charged probe biomolecule, as shown in FIG. 4B. By contrast, the electrical field applied to the surface of the gate adjacent to the second impurity region acts as a repulsion force to draw the negatively charged probe biomolecule, as shown in FIG. 4C. Therefore, in the case of the FET having the circular structure of the gate according to the present invention, since the gate region adjacent to the first impurity region is widened relative to the gate region adjacent to the second impurity region, the immobilization density of the probe biomolecule is very high.

Figure 5:
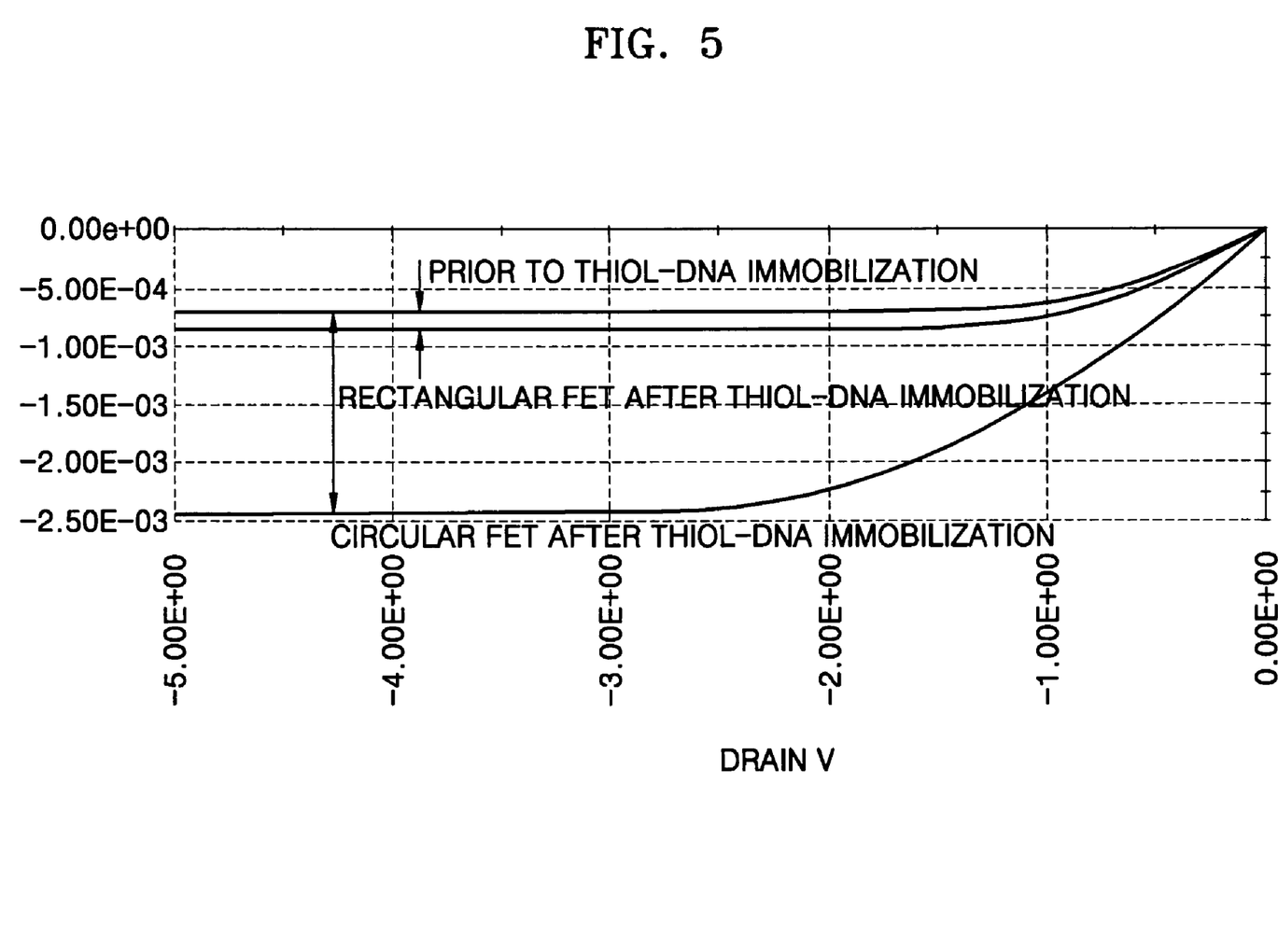
FIG. 5 is a view depicting electrical characteristics before and after an immobilization process of attaching a probe biomolecule to a surface of a gate with respect to a circular biomolecule FET according to the present invention and a conventional rectangular biomolecule FET.

FIG. 5 is a view depicting electrical characteristics before and after an immobilization process of attaching the probe biomolecule, for example, thiol-DNA, to the surface of the gate with respect to the circular biomolecule FET according to the present invention and the conventional rectangular biomolecule FET.

Explaining the conditions of the test, a biomolecule FET of a p-channel MOSFET type with first and second impurity regions doped with a p-type was used. A threshold voltage $V_{th}$ was −0.4 V, a width L of a gate was 200 μm, and a length thereof was 10 μm. A voltage $V_{gs}$ applied to the gate and the first impurity region was −2 V, and a voltage $V_{ds}$ applied to the second impurity region and the first impurity region was −0.4 V. The probe biomolecule to be attached to the surface of the gate was a composite probe DNA (thiol-DNA) (5'-thiol(C6)-GTTCTTCTCATCATC-3', 30 mer), and an immobilization time was 60 minutes.

W and L values were identical to each other in the conventional biomolecule FET and the biomolecule FET according to the present invention, and conditions of immobilization process of the probe biomolecule was equally applied.

Prior to carrying out the immobilization process, a current of −685 μA flowed through the biomolecule FET of the present invention and the conventional biomolecule FET. After the immobilization process, a current of −857 μA flowed through the conventional biomolecule FET, while a current of −2.451 mA flowed through the circular biomolecule FET of the present invention, even after the same immobilization process of the probe biomolecule. In other words, the current of the biomolecule FET according to the present invention is increased by about 10 times as high as that of the conventional biomolecule FET.

With the biomolecule FET of the present invention, since the structure of the gate is formed in a circular shape, the region adjacent to the first impurity region (source) is wider than the region adjacent to the second impurity region, thereby remarkably increasing the immobilization density of the probe biomolecule. Therefore, when detecting a level of hybridization of the probe biomolecule and the target biomolecule, a ratio of S/N is increased to remarkably increase its sensitivity.

While the present invention has been particularly shown and described with reference to exemplary embodiments depicted in the drawings, it will be understood by those of ordinary skill in the art that various changes and modifications in form and details may be made therein without departing from the spirit and scope of the present invention. Therefore, the true spirit and scope for protection of the present invention will be defined by the following claims.

What is claimed is:

1. A transistor based biomolecule FET comprising:
   a substrate;
   first and second impurity regions spaced apart and formed in a same side of the substrate;
   a gate formed on the substrate and being in contact with the first and second impurity regions; and
   a probe biomolecule attached to the gate,
   wherein a first region of the gate adjacent to the first impurity region is wider than a second region of the gate adjacent to the second impurity region so that a ratio of a circumferential length of the second region to width of the gate is greater than 10, the width of the gate being equal to a distance between the first and second regions of the gate.

2. The biomolecule FET of claim 1, wherein the gate and the first impurity region enclose the second impurity region in a circular shape.

3. The biomolecule FET of claim 1, wherein the first impurity region is a source, and the second impurity region is a drain.

4. The biomolecule FET of claim 1, further comprising a reference electrode formed on the gate for detecting a level of hybridization of the probe biomolecule and a target biomolecule.

5. The biomolecule FET of claim 1, wherein the substrate is doped with an n-type impurity, and the first impurity region and the second impurity region are doped with a p-type impurity.

6. The biomolecule FET of claim 1, wherein the biomolecule includes DNA, RNA, or protein.

7. The biomolecule FET of claim 1, wherein the gate includes
   an oxide layer;
   a poly-silicon layer formed on the oxide layer; and
   a gate electrode layer formed on the polysilicon layer.

8. The biomolecule FET of claim 1, wherein the ratio of width to length of the gate is between 10 and 30.

9. A transistor based biomolecule FET comprising:
   a substrate;
   first and second impurity regions spaced apart and formed in a same side of the substrate, and the first and second impurity regions doped with impurities of a polarity opposite to that of the substrate;
   a gate formed on the substrate and being in contact with the first and second impurity regions; and
   a probe biomolecule attached to the gate, wherein the gate is in contact with an outer upper portion of the second impurity region to enclose a region of the second impurity region, and the first impurity region encloses an outer lower portion of the circular gate, whereby a ratio of circumferential length of the second impurity region to width of the gate is greater than 10, the width of the gate being equal to a distance between the first and second impurity regions of the gate.

10. The biomolecule FET of claim 9, further comprising a channel having a desired width between the first impurity region and the second impurity region.

11. The transistor of claim 9, wherein the ratio of width to length of the gate is between 10 and 30.

* * * * *